United States Patent [19]

Madelaine et al.

[11] 4,277,682
[45] Jul. 7, 1981

[54] DEVICE FOR ANALYZING THE ACTIVITY OF A RADIOACTIVE AEROSOL AS A FUNCTION OF THE GRAIN SIZE DISTRIBUTION OF ITS PARTICLES

[75] Inventors: Guy Madelaine, Villebon sur Yvette; Michel Pourprix, L'Ha les Roses, both of France

[73] Assignee: Commissariat a l'Energie Atomique, Paris, France

[21] Appl. No.: 61,174

[22] Filed: Jul. 27, 1979

[30] Foreign Application Priority Data

Aug. 29, 1978 [FR] France ............................ 78 24885

[51] Int. Cl.$^3$ ............................................. G01T 1/18
[52] U.S. Cl. ..................................... 250/380; 250/385; 250/435
[58] Field of Search ................ 250/380, 379, 385, 374, 250/375, 364, 432 R, 435

[56] References Cited

U.S. PATENT DOCUMENTS

| 2,957,084 | 10/1960 | Marr et al. | 250/380 |
| 4,013,888 | 3/1977 | Macias et al. | 250/380 |

Primary Examiner—Davis L. Willis

[57] ABSTRACT

Device for analyzing the activity of a radioactive aerosol as a function of the grain size distribution of its particles of the type comprising a tight enclosure, means for circulating the aerosol through said enclosure and within the latter, a plurality of stages for collecting aerosol particles with a given grain size, each of the stages comprising an aerosol injection plate perforated by at least one calibrated opening and a collection plate for particles of a given grain size, wherein it comprises means for establishing an electric field between the injection and collection plates of each of the stages with a view to establishing an ionization current through a stage during the disintegration of the particles collected in the latter and means for measuring the ionization current of one of the said stages.

4 Claims, 1 Drawing Figure

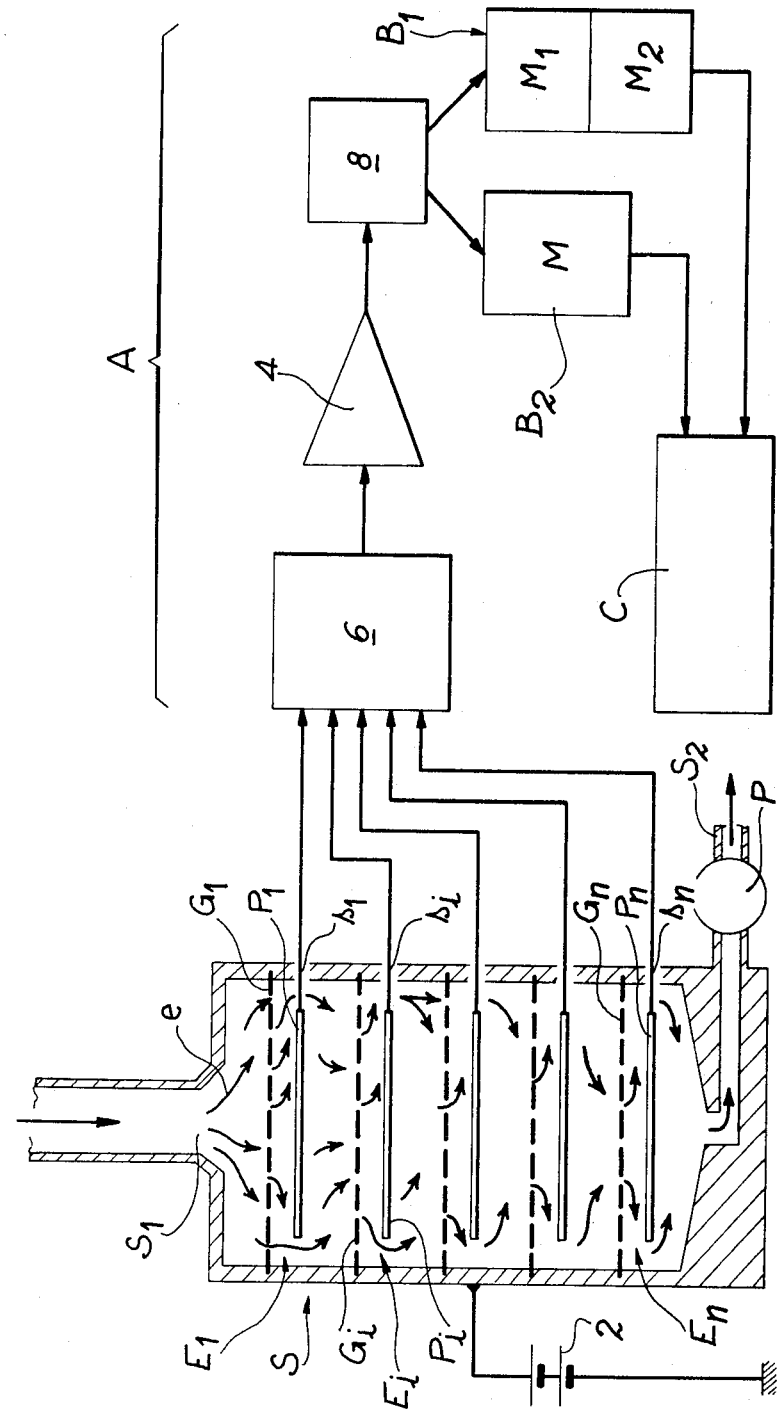

DEVICE FOR ANALYZING THE ACTIVITY OF A RADIOACTIVE AEROSOL AS A FUNCTION OF THE GRAIN SIZE DISTRIBUTION OF ITS PARTICLES

BACKGROUND OF THE INVENTION

The present invention relates to a device for analyzing the activity of a radioactive aerosol as a function of the grain size distribution of its particles.

This analyzer is more particularly suited to the rapid evaluation of the activity of inhalable particles suspended in the air of a room or the like which is liable to be contaminated. Thus, the penetration of the human organism via the respiratory tracts of the different constituent particles of an aerosol is a direct function of their grain size distribution. For this reason it is very useful to establish the spectrum of their activity as a function of their grain size in order to evaluate the contamination risk involved.

In order to analyze the activity of a radioactive aerosol as a function of the grain size distribution of its particles it is necessary to successively separate the aerosol particles into particle batches of a given grain size and to determine the activity of each of the particle batches.

It is conventional practice to use a device called a "cascade impacter" for separating the particles of an aerosol into particle batches of a given grain size. Within a tight enclosure such an impacter has a plurality of stages, each of which collects particles of a given grain size when an aerosol is put into operation in the enclosure, whereby each stage has an aerosol injection plate perforated by at least one calibrated opening and a particle collection plate. However, these "impacters" do not permit the direct measurement of the activity of the particles of one stage without manual intervention within the latter.

Thus, prior to the present invention it was necessary to dismantle the collection plate of one stage in order to measure, e.g. by means of a photomultiplier the radioactive activity of particles collected in said stage.

Thus, prior to the present invention it was not possible to carry out in complete safety and with adequate accuracy the analysis of the activity of a radioactive aerosol as a function of the grain size distribution of its particles.

BRIEF SUMMARY OF THE INVENTION

The object of the present invention is to provide a device for analyzing the activity of a radioactive aerosol as a function of the grain size distribution of its particles and which obviates the above-mentioned shortcoming.

This analyzer of the type comprising a tight enclosure, means for circulating the aerosol through said enclosure, and within the latter, a plurality of stages for collecting aerosol particles with a given grain size, each of the stages comprising an aerosol injection plate perforated by at least one calibrated opening and a collection plate for particles of a given grain size, wherein it comprises means for establishing an electric field between the injection and collection plates of each of the stages with a view to establishing an ionisation current through a stage during the disintegration of the particles collected in the latter and means for measuring the ionisation current of one of the said stages.

The analyzer as defined hereinbefore advantageously utilises the transformation of each of the stages of an impacter into an ionisation chamber. Thus, it provides the advantage of permitting a rapid and accurate measurement of the activity of particles of one stage without necessitating manual interventions within the latter.

It is therefore particularly suitable for monitoring and controlling the air of a room or the like which is liable to be contaminated.

It is pointed out that the device according to the invention makes it possible to analyze the $\alpha$ or $\beta$ activity of an aerosol.

According to a first embodiment of the device of the invention, more particularly intended for the measurement of low activities, the means for measuring the ionisation current of one of the said stages comprise current pulse counting means and means for connecting said counting means to one of the stages.

According to another embodiment of the device according to the invention used for measuring higher activities the means for measuring the ionisation current of one stage comprise means for measuring an average current and means for connecting said measuring means to one of the said stages.

According to a preferred embodiment of the device according to the invention permitting measurements in a wide range of activities the means for measuring the ionisation current of one stage comprise average current measuring means, current pulse counting means and means for connecting either the average current measuring means or the current plate counting means to one of the said stages.

DESCRIPTION OF THE DRAWING AND PREFERRED EMBODIMENTS

Other features and advantages of the present invention can be gathered more clearly from the following description of a non-limitative embodiment, with reference to the single drawing which shows an overall diagram of the analyzer according to the invention.

The attached drawing shows that the analyzer according to the invention substantially comprises an enclosure S for separating the particles of an aerosol into particle batches of a given grain size and a system A for determining the activity of each of the particle batches.

More specifically the separation enclosure S, equipped with means such as a pump P which is positioned downstream to establish an aerosol flow e between its inlet $S_1$ and its outlet $S_2$ is subdivided into a plurality of stages $E_1, E_i \ldots E_n$, each of which connects a particle batch of a given grain size.

Each stage $E_i$ comprises a plate or grating $G_i$ perforated by calibrated holes or openings through which the aerosol is injected into stage $E_i$ and a plate $P_i$ for collecting particles of a given grain size.

In such an enclosure S the particles strike against one or other of the plates $P_i$ in accordance with their inertia value in the corresponding stage. Thus, with enclosure S supplied with aerosol at a constant flow rate and gratings $G_i$ perforated by openings whose dimensions progressively decrease from stage $E_1$ to stage $E_n$ particle batches are collected in the stages, whose grain size progressively decreases from stage $E_i$ to stage $E_n$.

According to the essential feature of the invention one stage $E_i$ of the enclosure S is transformed into an ionisation chamber for the purpose of the direct measurement, via the above system A, of the activity of the particles deposited on plate $P_i$.

To this end for establishing an electric field between plate $P_i$ and grating $G_i$ of a stage $E_i$ gratings $G_i$ are connected to a power supply 2 and plates $P_i$ are connected to earth via system A for determining the activity of the particles of one of the stages $E_i$.

It can be seen from the attached drawing that system A essentially comprises an amplifier 4 for the current pulses obtained at the outlet $S_i$ of a stage $E_1$, said amplifier being connected to the stages $E_i$ via a switch 6, two current measuring systems $B_1$ and $B_2$ connected via a switch 8 to amplifier 4 and a system C for calculating the activity of the particles of one stage $E_i$.

More specifically the measuring system $B_i$ comprises means $M_i$ for shaping the current pulses obtained at the output of amplifier 4 and means $M_2$ for counting the shaped pulses, whilst measuring system $B_2$ comprises means M for measuring an average current.

The device shown in the drawing analyzes an aerosol in the following manner. The circulation of an aerosol through enclosure S by means of a pump P leads to each plate $P_i$ collecting a batch of aerosol particles with a given grain size.

Knowing that each disintegration of particles which occurs in the space between the plate and the grating produces within said space an ionisation which produces a current impulsion the determination by system A of the activity of the particles of a given stage $E_i$ will result either from the counting during a given time of the current pulses by means of system $M_2$ or the measurement during a given time of an average current by system M.

Obviously the measurement of the activity of collected particle batches necessitates a prior calibration of the device.

It should be noted that the device according to the invention can permit a sequential analysis of an aerosol.

For this purpose it is necessary to use on the one hand a sequential pump P permitting successive passages of different aerosol samples and, between two sample passages, the activity of the particles of each of the stages is measured. On the other hand it is possible to use means permitting the storage of the value of the activities measured after the passage of a sample and the differentiation between the activities measured at the end of two consecutive sample passages for the analysis of the activity of a sample.

The invention is not limited to the embodiments described and represented hereinbefore and various modifications can be made thereto without passing beyond the scope of the invention.

What is claimed is:

1. A device for analyzing the activity of a radioactive aerosol containing particles of different grain sizes, as a function of the grain size distribution of said particles, said device comprising a tight enclosure, means for circulating the aerosol through and within said enclosure, a plurality of stages defined within said enclosure, for collecting aerosol particles of varying grain size, each of said stages comprising an aerosol injection plate perforated by at least one opening calibrated to prevent passage of those of said particles having a grain size greater than a predetermined grain size and a collection plate for said particles, means for establishing an electric field between the injection and collection plates of each of said respective stages to establish an ionization current through each of said stages during the disintegration of the particles collected in a stage to be analyzed, and means for measuring the ionization current of each of said stages.

2. A device according to claim 1, wherein the means for measuring the ionisation current of any of said stages comprises current pulse counting means and means for connecting said counting means to any of said stages.

3. A device according to claim 1, wherein the means for measuring the ionisation current of any of said stages comprises means for measuring an average current and means for connecting the said measuring means to any of said stages.

4. A device according to claim 1, wherein the means for measuring the ionisation current of any of said stages comprise means for measuring an average current, current pulse counting means and means for connecting either the average current measuring means or the current pulse counting means to any of said stages.

* * * * *